(12) United States Patent
Eltorai et al.

(10) Patent No.: US 11,927,314 B2
(45) Date of Patent: Mar. 12, 2024

(54) HAND-MOUNTED ILLUMINATION METHOD, SYSTEM, AND DEVICES

(71) Applicant: Handlight Inc., Marlborough, MA (US)

(72) Inventors: Adam E. M. Eltorai, Marlborough, MA (US); Jeanette Numbers, Providence, RI (US); Seunghyuk Noh, Providence, RI (US)

(73) Assignee: Handlight, Inc., Marlborough, MA (US)

(*) Notice: Subject to any disclaimer, the term of this patent is extended or adjusted under 35 U.S.C. 154(b) by 0 days.

(21) Appl. No.: 17/970,006

(22) Filed: Oct. 20, 2022

(65) Prior Publication Data

US 2023/0040861 A1    Feb. 9, 2023

Related U.S. Application Data

(63) Continuation of application No. 17/487,656, filed on Sep. 28, 2021, which is a continuation-in-part of application No. 16/952,485, filed on Nov. 19, 2020, now Pat. No. 11,129,453.

(60) Provisional application No. 62/960,329, filed on Jan. 13, 2020.

(51) Int. Cl.
| | |
|---|---|
| *F21L 4/04* | (2006.01) |
| *F21L 4/08* | (2006.01) |
| *F21V 23/02* | (2006.01) |
| *F21V 23/04* | (2006.01) |
| *F21V 31/00* | (2006.01) |
| *F21Y 115/10* | (2016.01) |

(52) U.S. Cl.
CPC ............. *F21L 4/045* (2013.01); *F21L 4/085* (2013.01); *F21V 23/023* (2013.01); *F21V 23/0414* (2013.01); *F21V 31/005* (2013.01); *F21Y 2115/10* (2016.08)

(58) Field of Classification Search
CPC ......... F21L 4/045; F21L 4/085; F21V 23/023; F21V 23/0414; F21V 31/005
See application file for complete search history.

(56) References Cited

U.S. PATENT DOCUMENTS

2007/0147025 A1* 6/2007 Shirey ................ F21V 21/0885
362/109

* cited by examiner

*Primary Examiner* — Mary Ellen Bowman
(74) *Attorney, Agent, or Firm* — Armis IP Law, LLC

(57) ABSTRACT

A compact precision illumination source mounts on a finger of a user for providing localized illumination for precision tasks such as surgical procedures and other tasks performed in dark or confined spaces. A frame having a circular or arcuate shape engages the finger, and secures an enclosure having a small but powerful bright, light focused on a predetermined region defined by the end of the digit that is likely the activity region for an instrument grasped by the digit. The frame engages a charge module for aligning external conductors for recharging a power supply in the illumination source.

23 Claims, 12 Drawing Sheets

HAND-MOUNTED ILLUMINATION METHOD, SYSTEM, AND DEVICES

RELATED APPLICATIONS

This patent application is a Continuation (CON) under 35 U.S.C. § 120 of U.S. patent application Ser. No. 17/487,656, filed Sep. 28, 2021, entitled "HAND-MOUNTED ILLUMINATION METHOD, SYSTEM AND DEVICES, which is a Continuation-in-Part under 35 U.S.C. § 120 of U.S. patent application Ser. No. 16/952,485, filed Nov. 19, 2020, entitled "HAND-MOUNTED ILLUMINATION METHOD, SYSTEM AND DEVICES," now U.S. Pat. No. 11,129,453, which claims the benefit under 35 U.S.C. § 119(e) of U.S. Provisional Patent App. No. 62/960,329, filed Jan. 13, 2020, entitled "METHOD AND DEVICES FOR MEDICAL, SURGICAL and DENTAL PROCEDURE LIGHTING," and all incorporated herein by reference in entirety.

BACKGROUND

Portable light sources for specialized and task lighting contexts are employed wherever fixture lights are impractical or unnecessary. A need for a small portable illumination device has, for some time, been satisfied by a breadth of simple devices commonly referred to as "flashlights."

As an example, surgical environments depict a context where task lighting is paramount. Surgical environments generally require a sterile field to prevent infection and ample lighting to enhance a visual region for the precise manipulation of human tissue. A typical operating room employs a well-defined array of fixtures and procedures for maintaining a sterile environment and ensuring a robust infrastructure of instruments and utilities such as gases, suction, medication, electrical and pneumatic resources, in addition to lighting. Modern Operating Rooms (ORs) define a highly evolved and specialized environment for ensuring effective medical care.

SUMMARY

A compact precision illumination source mounts on a digit of a user for providing localized illumination for precision tasks. A frame having a circular or arcuate shape engages the digit, and secures an enclosure having a small but powerful, bright light focused on a predetermined region defined by the end of the digit that is likely a region of activity for grasped by the digit. Low cost elements such as coin cell batteries and LED (Light Emitting Diodes) contribute to the efficacy of a single-use lighting appliance energized by an unretractable switch or contact closed by device activation. As with many surgical accessories, single-use materials and accessories mitigate cross contamination from other patients or procedures, and cost mitigation in producing single-use devices contributes to feasibility of use.

Configurations herein are based, in part, on the observation that utility lighting for precision manual tasks increases speed, efficiency and accuracy by reducing eye strain and facilitating hand-eye coordination. Unfortunately, conventional approaches to utility lighting in medical and non-medical contexts suffer from the shortcoming that power and space constraints oppose ideals of providing bright illumination in tight, confined spaces as is often the case in a surgical field. Lighting sources need to be either tethered to a power source or rely on onboard batteries; the former interferes with movement and the latter is constrained with a volume of charge material having longevity to span a possibly undetermined duration of a surgical procedure.

Accordingly, configurations herein substantially overcome the above described shortcomings by providing a compact, single-use digit (finger) mounted light aimed generally at the business end of a hand-held instrument and powered by on-board cells stored in an enclosure adjacent a pair of focused LED elements for illuminating the work area, such as a surgical field, of the instrument. The digit mounted illumination source generates and focuses light to mitigate diffusion losses when light is spread over a larger area. Rather, the illumination source is immediately proximate to an object of operator dexterity.

In a basic configuration, a portable, self-contained personal lighting apparatus includes a body having an illumination source and a power supply for illuminating the illumination source. A plurality of deformable prongs extends from the body, such that the prongs are adapted for forming an annular, concave form for resiliently converging around a human digit in a biased clamping or compression fit. The illumination source is then focused on a distal region in a direction defined by the human digit around which the prongs engage, such as a region around a tip of the outstretched digit for lighting a task performed by the finger.

In a particular configuration, a surgical illumination configuration may be provided as disclosed herein, and includes a body having an enclosure and an annular frame. The annular frame has two prongs extending in an arcuate manner from the enclosure, such that the prongs are adapted to engage an index or other finger similar to a jewelry article. The enclosure includes a lighting element, a power supply for powering the lighting element, and a tray for containing the lighting element. The tray is a self-contained assembly including conductive members between the lighting element and power supply for energizing the lighting element. A void on the enclosure is adapted to receive the tray via slidable engagement, such that engagement establishes electrical communication between the power supply and the lighting element as the tray makes a single-use combination.

BRIEF DESCRIPTION OF THE DRAWINGS

The foregoing and other objects, features and advantages of the invention will be apparent from the following description of particular embodiments of the invention, as illustrated in the accompanying drawings in which like reference characters refer to the same parts throughout the different views. The drawings are not necessarily to scale, emphasis instead being placed upon illustrating the principles of the invention.

DETAILED DESCRIPTION

Depicted below is an example of various configurations of the single-use surgical utility light. Several views and arrangements are shown; other embodiments may be apparent to those of skill in the art by slight variations to the form factor and electrical circuit as shown.

Configurations described below disclose and illustrate a task lighting feature applicable in many contexts based on the small size, finger mount and self-contained power due to a low power draw that need not employ large batteries. A surgical example is discussed as an illustrative case. Such a surgical use invokes many of the features, such as single usage, sterile presentation and task-focus, however many contexts do not require or impose all these constraints. Many tasks are not restricted to sterile instruments, and for the same reason single use enforcement can be waived. Example uses and applications to such non-medical applications may include operation as flashlights, headlights, lamps, torches, searchlight, spotlights, lanterns, etc.; use in fields such as arts, crafts, repair, fishing, camping, hiking, running, nocturnal contexts, biking, vehicle maintenance, around the house, visualization, climbing, spelunking, photography, outdoor sports, hunting, boating, walking, diving, ambulating, manufacturing, warehousing, excavation, electricity generation and power plant operations, custodial work, farming, commercial fishing, logging, landscaping, pest control, food processing, oil field work, waste collection and disposal, recycling, construction, maintenance, shipping, driving, trucking, fashion, orienteering, skiing, backpacking, mountaineering, mountain biking, mining, search & rescue, caving, cataphiles, trouble lights, entertainment, indicators, lighting, communication, signaling, illumination, measuring and interacting, machine vision, biological detection, remote controls, sensor system, safety lamps, wheat lamps, theatrical, cinematic, emergency light, reading, working, nightlight, pointing, decorative, navigation, automotive-related, aviation-related, lamp, laser pointer, polilight, safelight, slit lamp, desk lighting, industry, research, leisure, weapons systems, pet-related, raves, concerts, dance clubs, germicidal, grow light, infrared lamp, strobe, health benefits, safety device, protective gear, rescue equipment, boating, law enforcement, travel, inspection, engineering, instrumenting, tinkering, reading, inspecting wounds, visualize mouth & throat, assess pupil response, view into small openings, look under poorly lit areas, plumbing, veterinary applications, dentistry, hands-free applications, military, control device, task lighting, cameo lighting, photography, security, electrician, manual labor, cooking, machinery and others.

Figure 1:
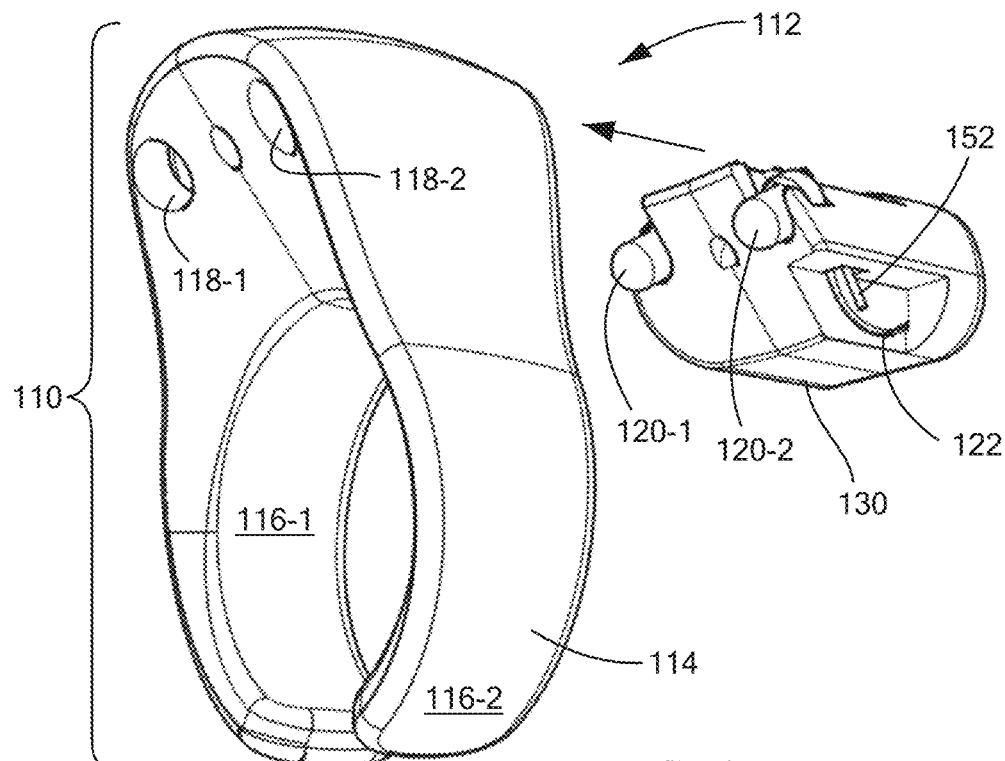
FIG. 1 is a frontal perspective view of the enclosure and tray of surgical illumination device viewed from a left side.
Figure 2:
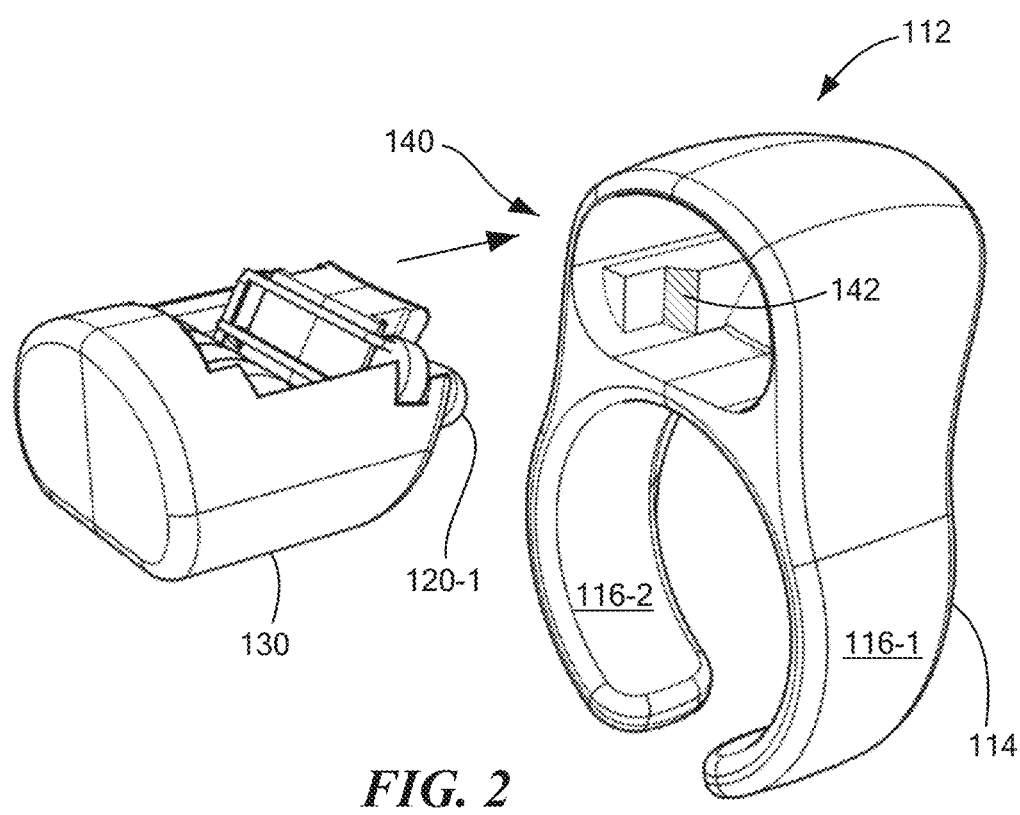
FIG. 2 is a rearward perspective view of the enclosure and tray of the surgical illumination device viewed from a right side.

FIG. 1 is a frontal perspective view of the enclosure and tray of the surgical illumination device viewed from a left side, and FIG. 2 is a rearward perspective view of the enclosure and tray of the surgical illumination device viewed from a right side. Referring to FIGS. 1 and 2, the surgical illumination device 100 includes a body 110 having an enclosure 112 and an annular frame 114. The annular frame has two prongs 116-1 . . . 116-2 (116 generally) extending in an arcuate manner from the enclosure 112, such that the prongs 116 are adapted to engage an elongated member such as the index finger, wrist or other digit of the wearer. The elongated prongs may be of any suitable length to engage, by frictional or compressive bias, or may form a loop.

The enclosure 112 includes on or more lighting elements 120-1 . . . 120-2 (120 generally), a power supply 122 such as a battery for powering the lighting elements 120, and a tray 130 for containing the lighting elements 120. Conductive members 152 extend between the lighting elements 120 and power supply 122 for energizing the lighting element, shown in FIG. 3B below. A void 140 is adapted for slidable engagement with the tray 130, such that the slidable engagement establishes electrical communication between the power supply 122 and the lighting elements 120. A tapered surface 142 may facilitate attachment and locking the tray 130 in the void 140, and may provide electrical actuation for the lighting elements 120, discussed further below. Apertures 118-1 . . . 118-2 (118 generally) in the enclosure 112 align with the lighting elements 120 upon insertion for allowing illumination from the enclosure 112. The power supply 122 is disposed in the tray 130, and further includes an actuator 150 responsive to slidable insertion of the tray 130 into the void 140 for establishing electrical communication. Any suitable mechanism adapted to close (contact) the circuit and power the lighting elements 120 may be provided.

In a first configuration, the device is configured for medical applications as a single use device in sterile environments. The hand light could, of course, be sterilized for subsequent medical use, or employed in non-sterile environments. Alterations for battery removal or rechargeability may, of course, be provided.

Figure 3A:
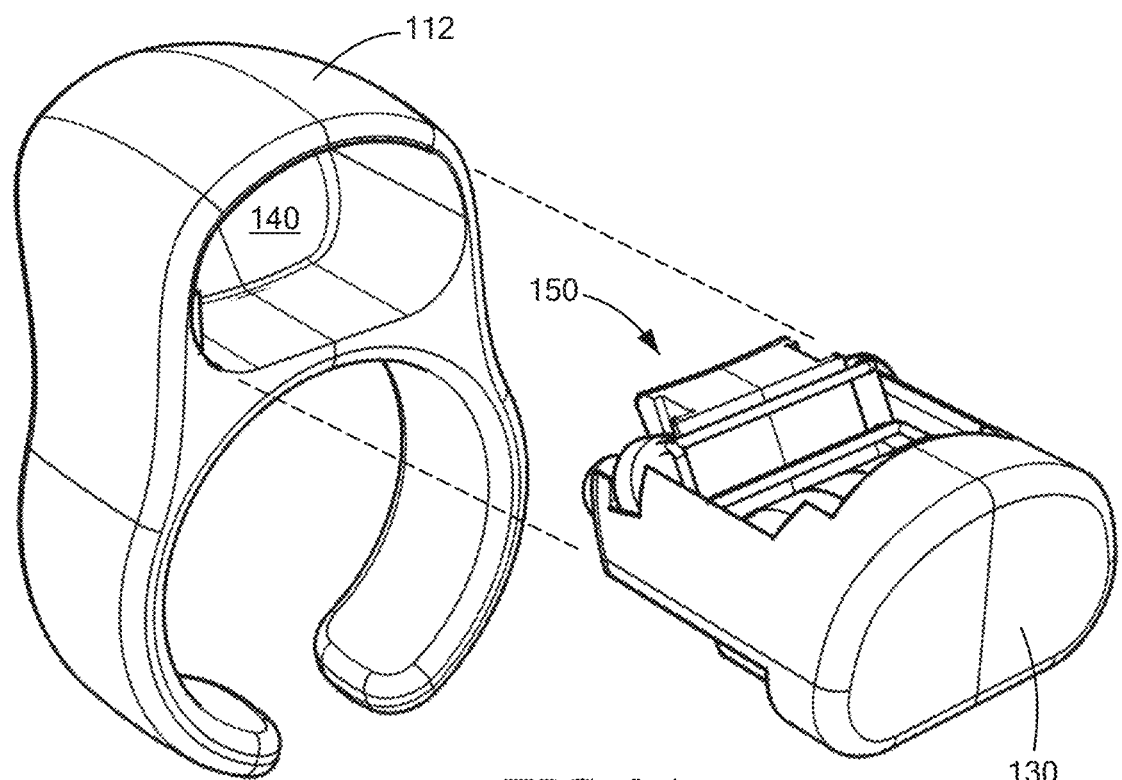
FIGS. 3A and 3B depict circuit operation for the surgical illumination device.
Figure 3B:
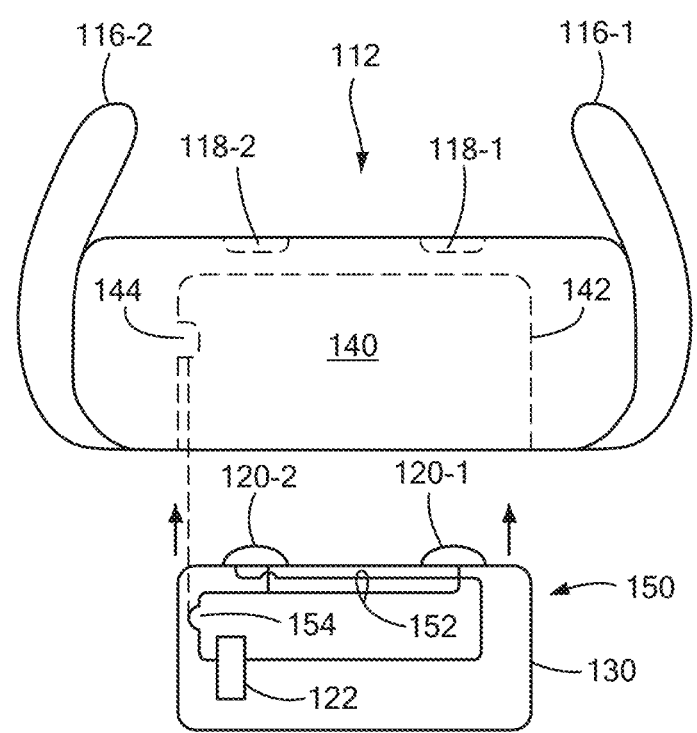

FIGS. 3A and 3B depict circuit 150 operation for the illumination device 100. As the tray 130 slides into the void 140 for device activation, electrical communication between the power supply 122 and lighting elements 120 is established. Any suitable mechanism may be employed, such as a mechanical switch, biased contact, conductive surfaces, inductive coupling, magnetic coupling, or other suitable approach that close (energize) the electrical circuit based on insertion of the tray 130.

The circuit 150 need not encumber the tray 130 with excessive components. The power supply 122 may be a coin cell battery, rechargeable cell or other source. Conductive members 152 such as wires or traces couple the positive and negative terminals of the power supply 122 to the respective terminals of the lighting elements 120, shown as adjacent LEDs 120-1 and 120-2. Any suitable number of lighting elements may be employed based on space constraints; LEDs provide a low power drain which is matched to a longevity of the power supply, and should last a minimum of 4-6 hours but could easily extend to 10 hours for a longer surgical procedure.

The circuit 150 further includes a switch 154, responsive to the engagement of the tray 130 for establishing the electrical communication. The switch 154 may be aligned to engage a protrusion 144 or tapered surface 142 within the void 140 for closing (activating) the circuit as the tray 130 is inserted. The void 140 has a perimeter 142 based on and aligned in close tolerance to the tray 130 size, such that slidable insertion into the enclosure draws the tray adjacent the void 140 interior for causing contact or interference with surface features or aberrations such as the protrusion 144 for actuating the switch 154.

Alternative configurations may replace the switch with a removable tab such as a plastic strip or insulating member disposed biased between the battery and a spring loaded contact may also be employed. The removable tab is disposed to maintain an open circuit by preventing current flow from the battery, and closing the circuit for energizing the lighting element upon removal of the tab. Inaccessibility of the tray or battery provides enforcement of the single-use provision for medical uses, as usage time is therefore limited to the battery life.

The switch may be integrated with a spring biased element for restraining the battery. Conductive members 152 may include a spring biasing for retaining the battery in a conductive manner. The same spring biasing may provide the undetachable engagement by slidably traversing the tapered surface 142, deforming and compressing against the tapered surface, and releasing or "snapping" into a latched arrangement after traversing the tapered side.

Figure 4:
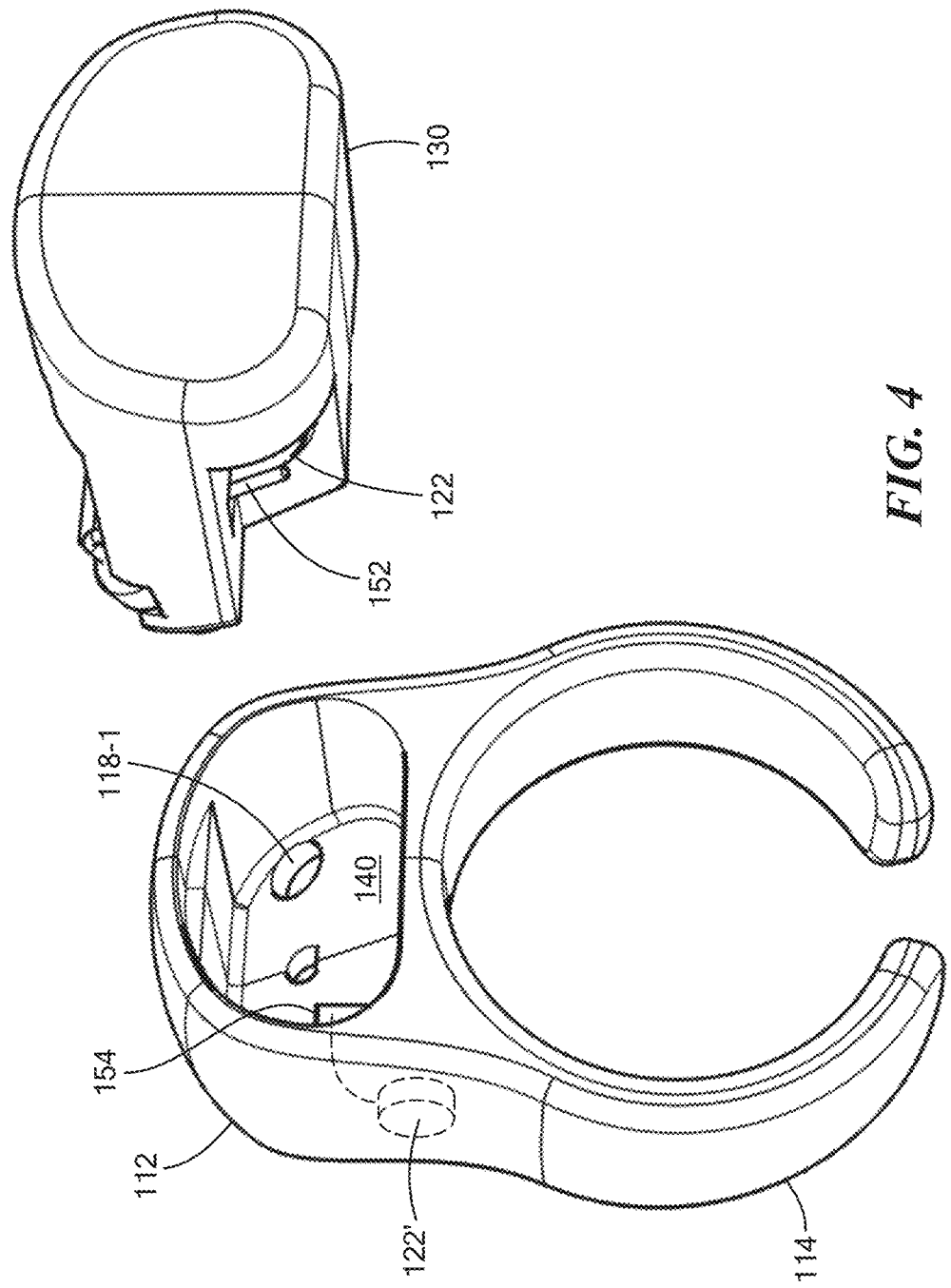
FIG. 4 is a perspective view of the left side of the enclosure and tray of the surgical illumination device viewed from an underside perspective.

FIG. 4 is a perspective view of the left side of the enclosure and tray of the surgical illumination device viewed from an underside perspective. Insertion of the tray 130 into the void 140 may also establish electrical power to the lighting elements based on a power source 122' in the enclosure 112, as well. Alternate approaches for closing the circuit 150 and energizing (powering) the lighting elements 120 upon tray 130 insertion may include a conductive surface on the tray 130, for example. The conductive surface is may attached or connect to the conductive elements 152, and is disposed for slidably engaging a complementary conductive surface on an interior surface of the void, such that slidable engagement of the conductive surface and the complementary conductive surface closes an electrical connection for energizing the lighting elements 120. The alternate power supply 122' in the enclosure 112 energizes the conductive surface; complementary ground connections are also provided.

Figure 5A:
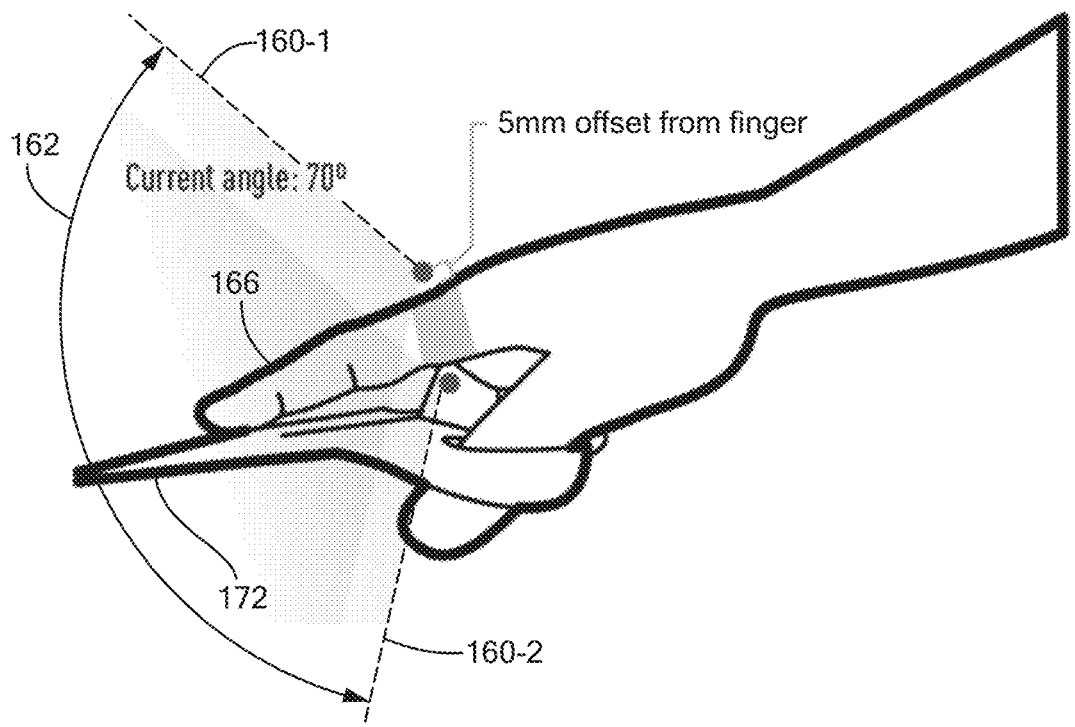
FIGS. 5A and 5B show a projection angle defining a focus of the lighting element in the device of FIGS. 1-4.
Figure 5B:
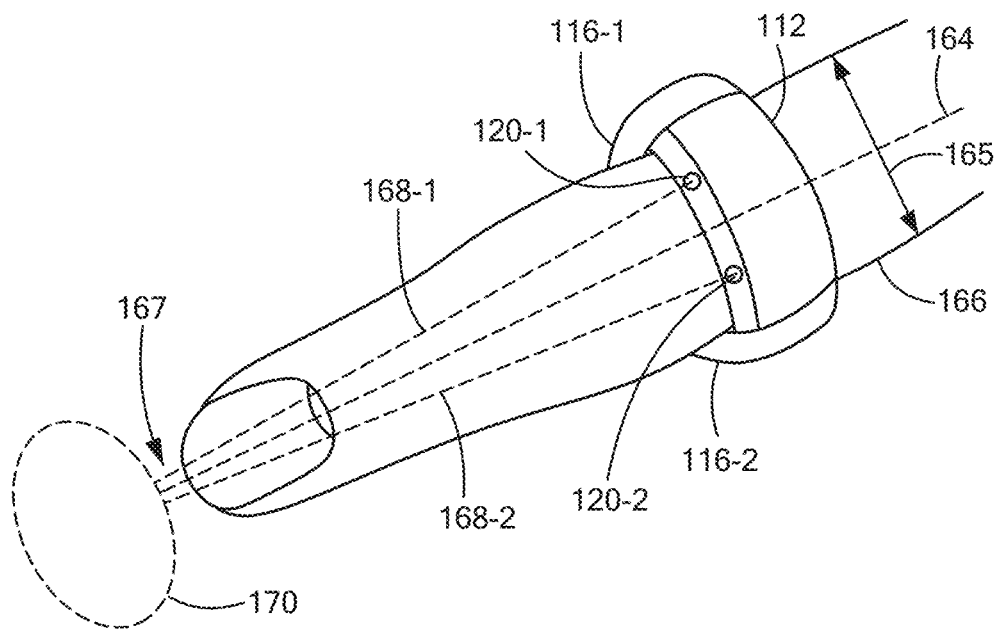

FIGS. 5A and 5B show a projection angle defining a focus of the lighting element in the device of FIGS. 1-4. Referring to FIGS. 1-5B, the lighting elements 120 define a projection angle 162 defined by dotted lines 160-1, 160-2. The projection angle 162 is based an axis 164 extending longitudinally through the engaged elongated member 166 for focusing on a distal end 167 of the elongated member 166. A breadth of the projection angle 166 depends on a periphery of the lighting elements 120, and a beam focus 168-1, 168-2 (168 generally) corresponding to a direction of strongest illumination from each respective lighting element 120, generally around a center of the projection angle 162. The beam focus 168 converges in a work region 170 which is based on activity of a surgical instrument 172 in the surgical field.

The elongated member 166 is expected to be defined by a human digit and the prongs 116 are opposed by a difference less than a diameter 165 of the elongated member 166. Since the light is directed slightly down and in front of the enclosure, an index finger is likely to be used due to the increased dexterity for the task at hand. The elongated members may also engage or wrap around a different carrier such as a wrist or arm of the wearer. The prongs 116 therefore include a deformable material for compressing the prongs in opposed directions for disposing the prongs 116 at a distance providing a frictional engagement with the elongated member 166. Resiliency of the deformable material biases the prongs against the elongated member 166, such that the prongs 116 retain the enclosure 112 by a bias against the elongated member 166. In alternate arrangements, the 116 prongs may have a closure defining a circular shape adapted for slidable communication with the elongated member, thus securing the enclosure as a ring of jewelry is frictionally secured around a finger.

Figure 6:
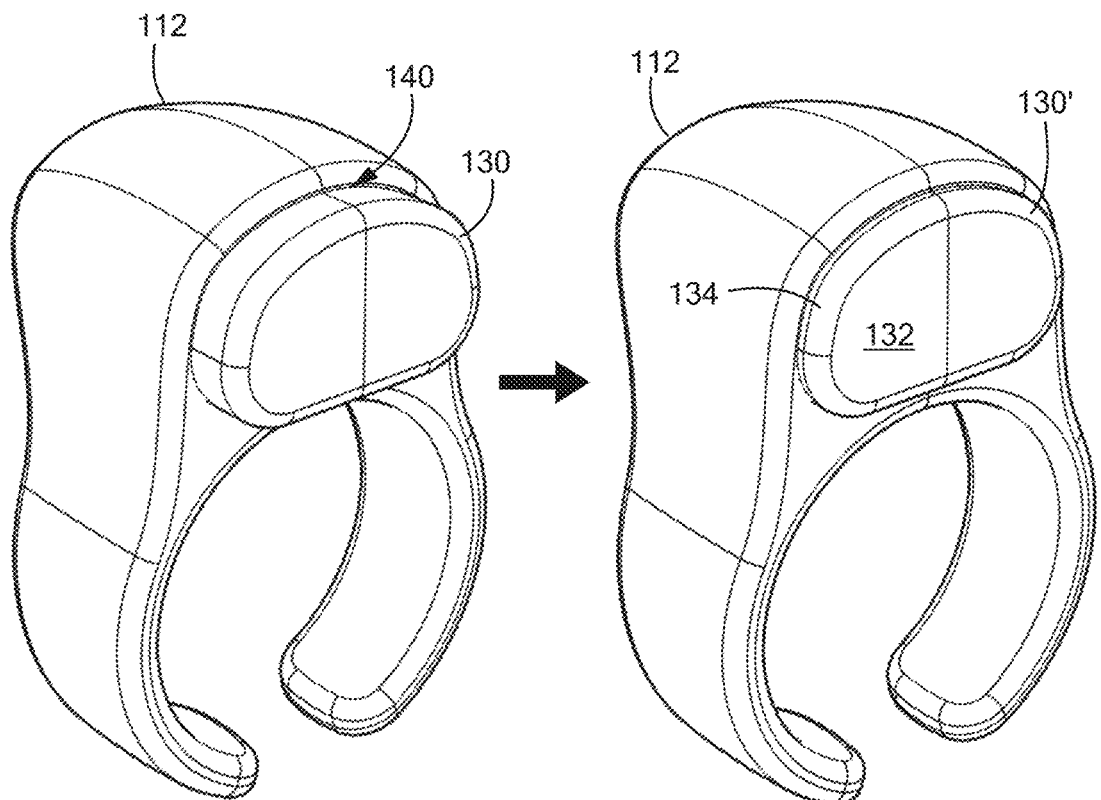
FIG. 6 shows a transition of the tray to an engaged, undetachable orientation.

FIG. 6 shows a transition of the tray 130 to an engaged, undetachable orientation. Referring to FIGS. 1-6, the tray 130 engages the void 140 in an undetachable manner, once the tray 130 fully engages the void 140, actuating the switch 154 and aligning the lighting elements 120 with the apertures 118. The engaged tray 130' remains secured and undetachable for enforcing the single-use provision of the device 100. No tabs, ridges or engaging surfaces are provided on the exposed tray panel 132. A tapered edge 134 aligns to provide a generally smooth, gently angled transition for resisting prying or interference with the now permanent tray 130' engagement with the enclosure 112. The tray 130-void 140 engagement may further include latch actuated by the tapered surface 142 for engaging the tray 130 in an undetachable manner upon insertion into the void 140.

For example, a deformable protrusion may extend from the tray, such that the deformable protrusion is disposed for slidable communication with the tapered surface 142. Upon tray 130 insertion, the deformable protrusion returns to an undeformed state to define a latching, interference fit with the enclosure 112 for preventing tray withdrawal.

Figure 7:
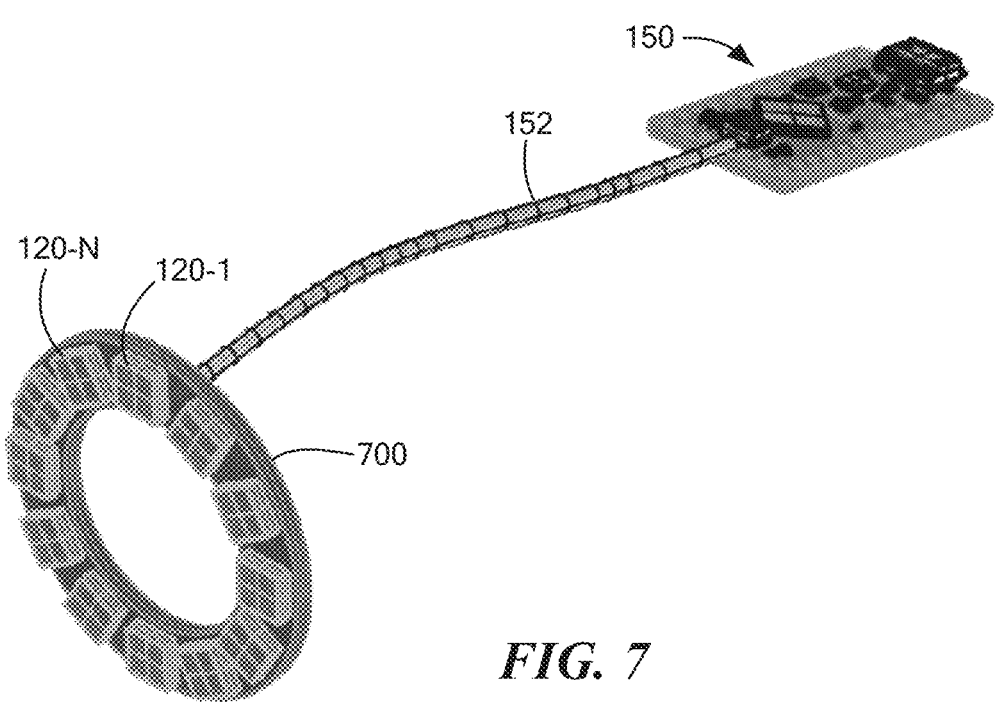
FIG. 7 shows an alternate configuration having the lighting elements arranged in a circumferential manner.

FIG. 7 shows an alternate configuration having the lighting elements arranged in a circumferential manner. A circular array 700 defines a mounting for lighting elements 120-1 . . . 120-N. The circuit 150 attaches to the circular array 700 via conductive members 152. The circular array 700 may be frictionally engaged around the elongated member 166.

Figure 8:
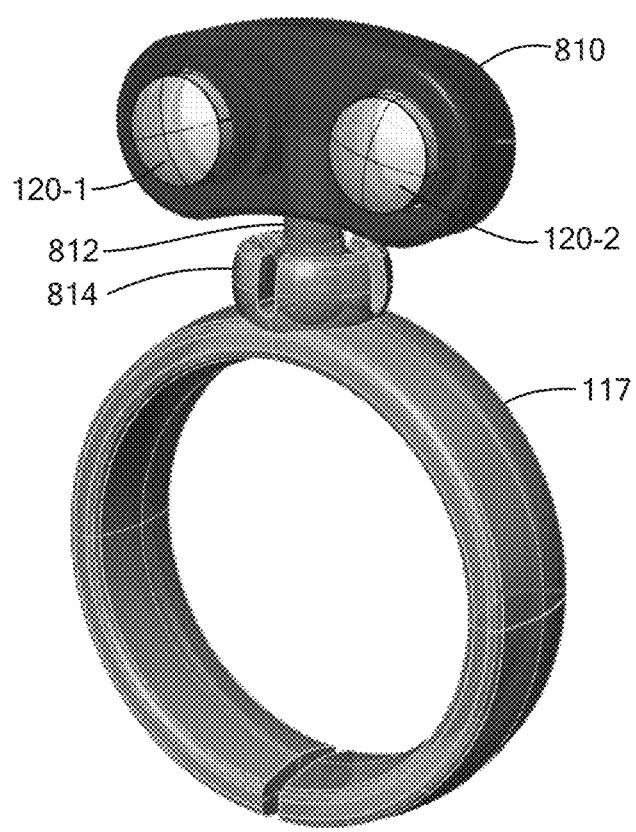
FIG. 8 shows an alternate configuration for varying the projection angle of the device of FIGS. 1-4.

FIG. 8 shows an alternate configuration for varying the projection angle of the device of FIGS. 1-4. In FIG. 8, the prongs 116 form a complete circular frame 117 as a jewelry item might fit. Lighting elements 120 reside in a pivoting attachment 810 secured to the circular frame 117 by a ball 812 and socket 814 arrangement.

Figure 9:
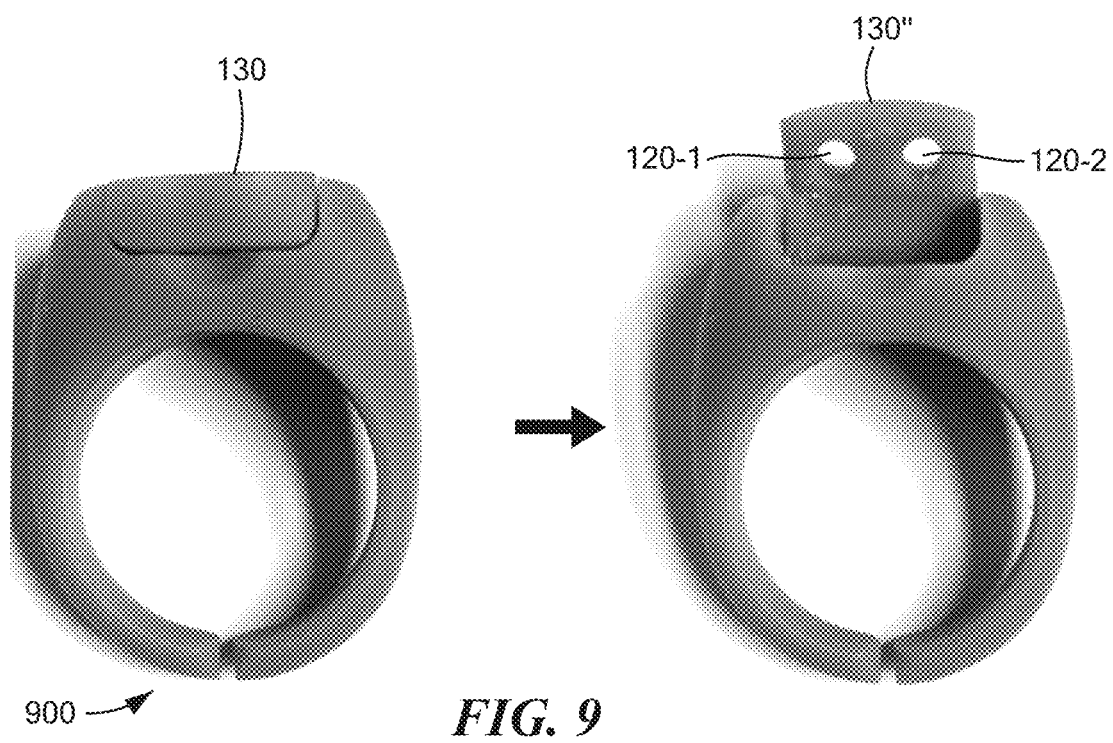
FIG. 9 shows an alternate configuration for concealing and altering the projection angle as in FIGS. 1-4.

FIG. 9 shows an alternate configuration for concealing and altering the projection angle as in FIGS. 1-4. FIG. 9 shows a device 900 hinged tray 130 that transitions to an open position 130'' to expose and position the lighting elements 120. The hinge allows adjustment of the projection angle 162 to suit the task at hand.

In alternate configurations, the surgical illumination device provides a general utility light by relaxing the single-use feature. This may be provided by a detent or hook on the tray for power supply 122 refresh (battery replacement). Alternatively, the power supply may be a rechargeable (lithium-ion or other battery chemistry) cell. Usage in a common (non-sterilized/operating room) context may of course be a popular usage context and need not invoke the single-use provision. A rechargeable and/or replaceable battery is particularly beneficial. In the case of a replaceable battery, the tray need not be locking, but rather provides battery access. In a rechargeable configuration, an electrical recharge connection is included. A USB (Universal Serial Bus) socket or similar connection for miniature and personal electronic devices may be employed.

FIGS. 10A-15B show one alternate configuration including a rechargeable power supply for repeated use. Outside of an operating room context, where single-use criteria is commonplace, the device need not be discarded after only one use. A reusable configuration includes a rechargeable battery, charging connection and power switch, all of which are hermetically sealed to waterproof the enclosure and allow for a high temperature wash for sterilization. The reusable device can be used in either medical or non-medical contexts, for example the liquid tolerant design is amenable to rugged environments where the device might be exposed to harsh chemicals and dust.

Figure 10A:
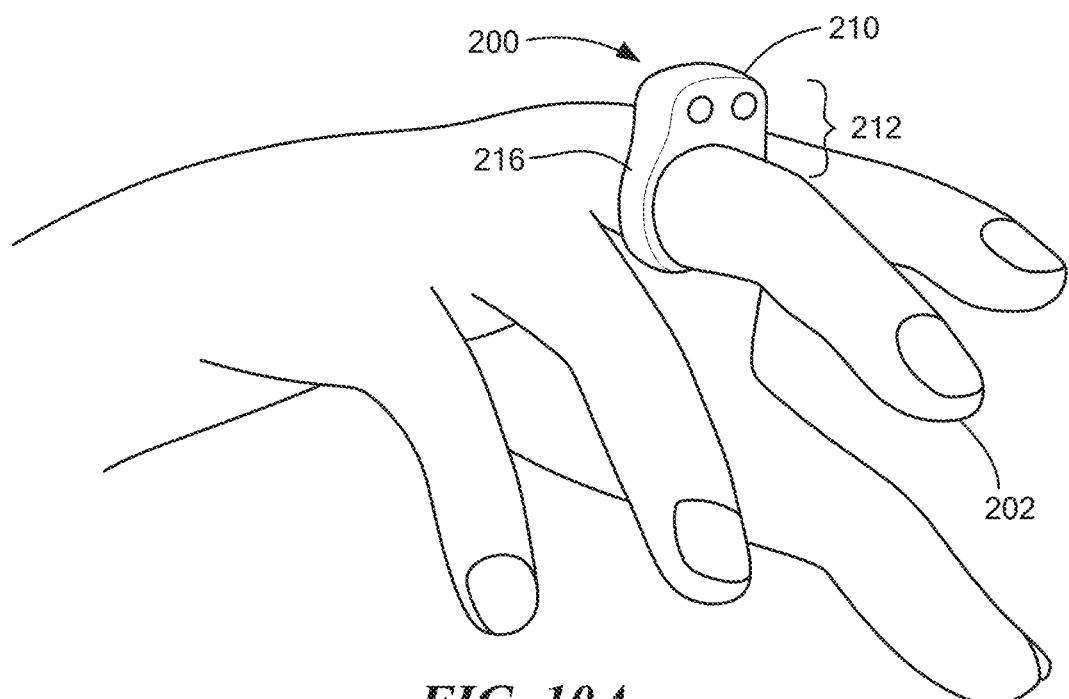
FIGS. 10A-10B shows a perspective view of a reusable, rechargeable configuration of the device of FIG. 1.
Figure 10B:
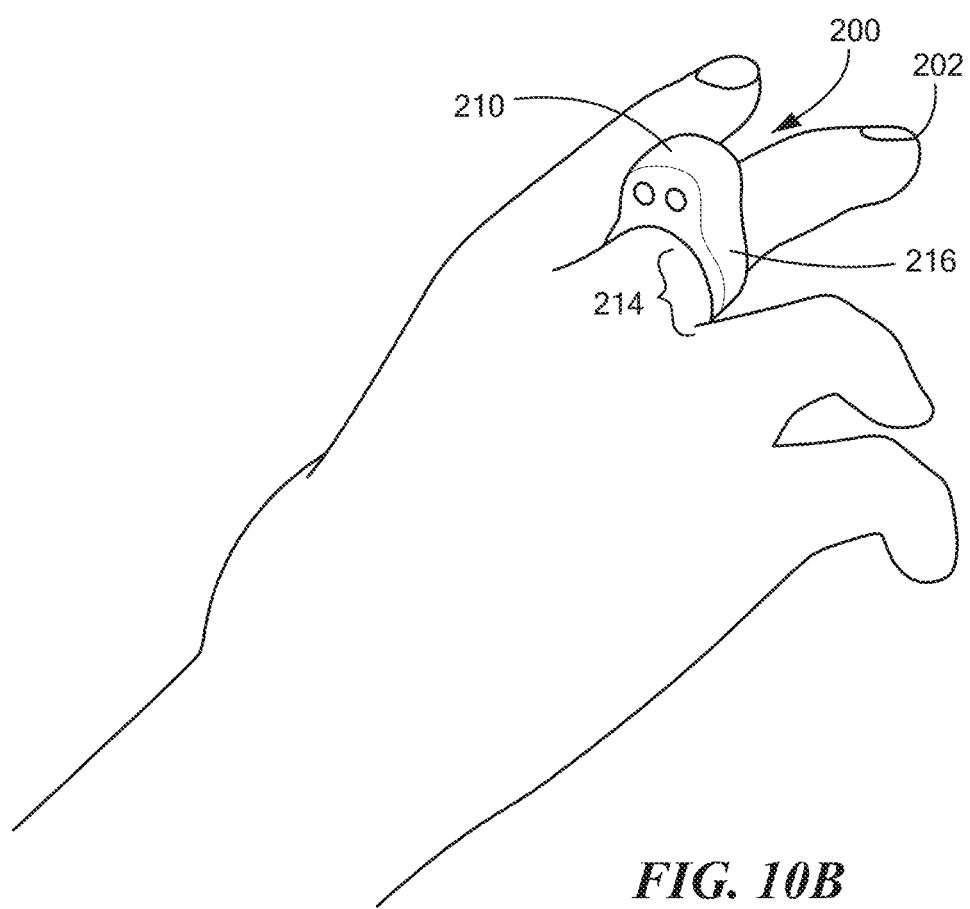

FIGS. 10A and 10B show a perspective view of a reusable, rechargeable configuration of the device of FIG. 1 and deployed on a user's digit. Referring to FIGS. 10A and 10B, the finger-mounted, rechargeable, sterilizable illumination device 200 includes a body 210 having an enclosure 212 and an annular frame 214. The annular frame has one or more elongated prongs 216 extending in an arcuate manner from the enclosure 212, collectively adapted to engage a human digit 202, typically as a pair 216-1 ... 216-2 (216 generally).

The enclosure 214 includes one or more lighting elements 120, and a power supply connected to the lighting element for energizing the lighting element, in which the power supply is defined by a rechargeable storage element (secondary battery) rather than a single use battery. Shown further below are an external conductor connected to the power supply for contact with an electrical source for recharging.

Alternate arrangements may, of course, employ a single use battery, such as in the single use configuration discussed above. Further, the enclosure has a chemical and solvent resistant surface that is amenable to high temperature cleaning and sterilization without compromising the waterproof seal and compromising the electronic elements. The enclosure and prongs have a surface responsive to such cleaning, sterilization and/or detergents. The power switch and rechargeable connections likewise enjoy a waterproof seal for preventing fluid infiltration.

Figure 11:
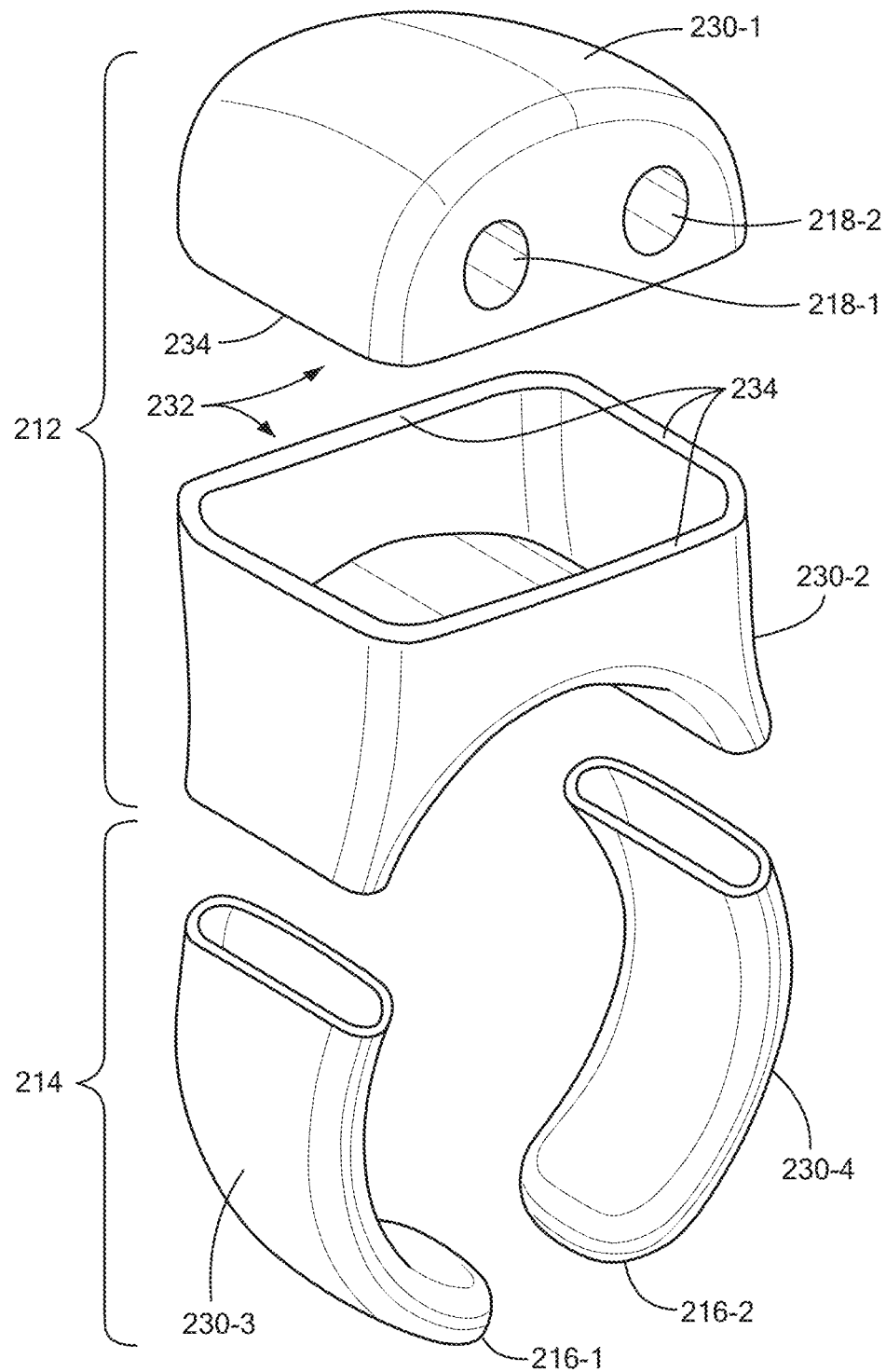
FIG. 11 shows an exploded view of portions defining the body of the device of FIGS. 10A-B.

FIG. 11 shows an exploded view of portions defining the body of the device 200 of FIG. 10. The exploded view of FIG. 11 depicts use of a hermetic, or waterproof, seal between the lighting element 220, the external conductors and the enclosure 212. The enclosure 212 includes a plurality of molded portions 230-1 ... 230-4 (230, generally). The size and arrangement of the molded portions may vary based on manufacturing requirements and capabilities to form the entire body 210, and need not be exactly as shown. For example, molded portions may be formed homogeneously with at least one of the prongs. The example of FIG. 11 includes a top enclosure portion 230-1, a bottom enclosure 230-2 portion, and right and left prong portions 230-3, 230-4, respectively. The enclosure portions form a void 232 for encapsulating the power supply, wires/conductive members and other electrical elements for energizing the lighting elements, similar to the tray of FIGS. 3A and 3B. Whatever architecture of the portions 230 is employed, the waterproof seal incorporates a fused seam 234 at the juncture between each molded portion adjacent the void 232, to restrict against fluid infiltration.

One or more of the molded portions includes an aperture 218 for the lighting elements 220. Typically a pair of apertures 218-1 ... 218-2 (218 generally) provides redundancy and focus, as shown in FIG. 5B. The lighting elements 120 are convex LEDs or similar rounded shape that may establish a compression fit or sealed junction between the aperture 218 and the lighting element 220. A well defined aperture diameter, slightly smaller than a convex LED surface, establishes a waterproof (fluid) seal when pressed tightly against the aperture 218 from within the void 232. Alternatively, a viscous, deformable, or elastic material such as that employed for the fused seam 234 may surround the apertures 218 for providing the waterproof seal.

Figure 12:
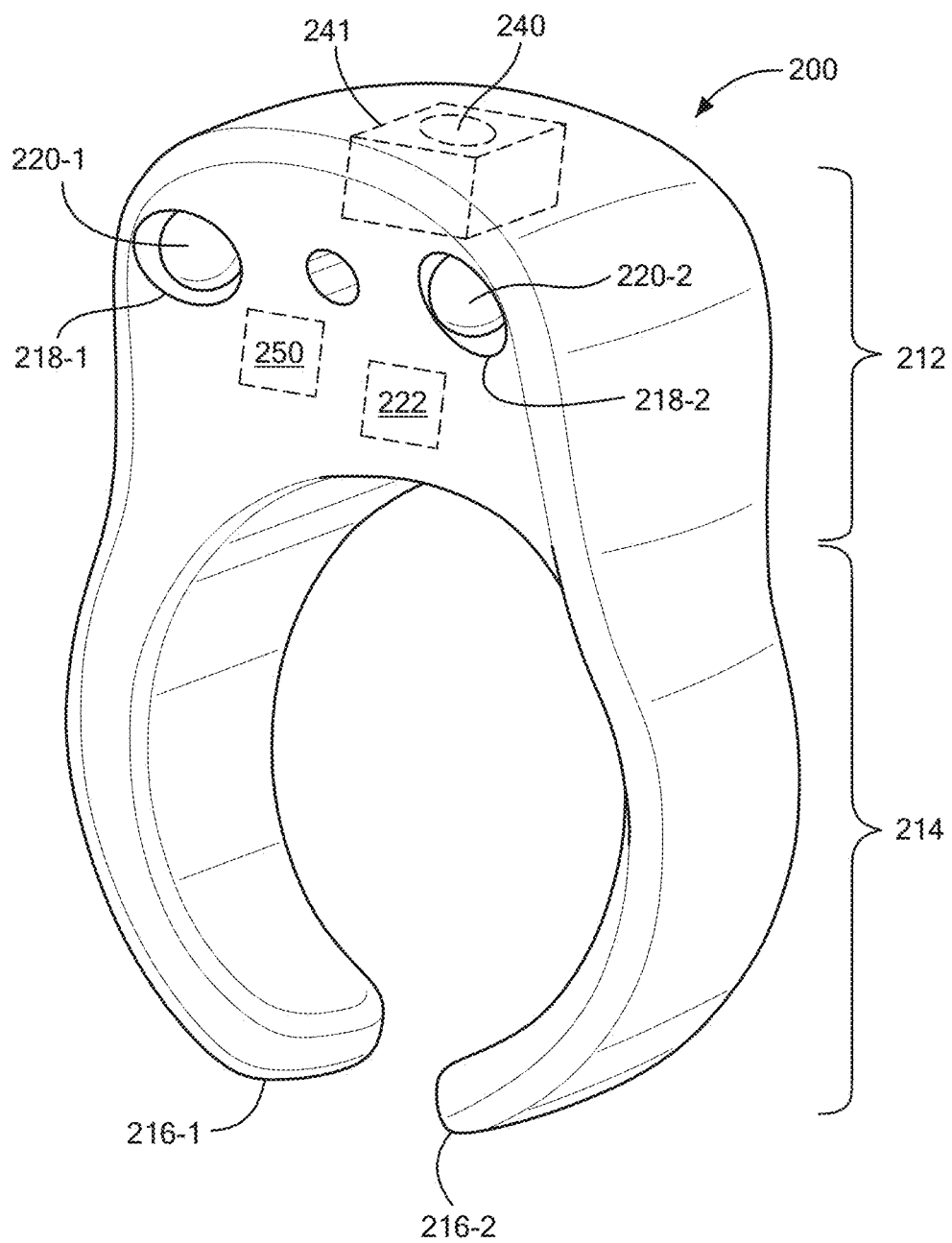
FIG. 12 shows a front elevation of the device of FIGS. 10A and 11.

FIG. 12 shows a front elevation of the device 200 of FIGS. 10A-B and 11. Dotted outlines depict placement of a switch 240, power supply 222, and charging port 250 for external connection to an electrical source.

Figure 13A:
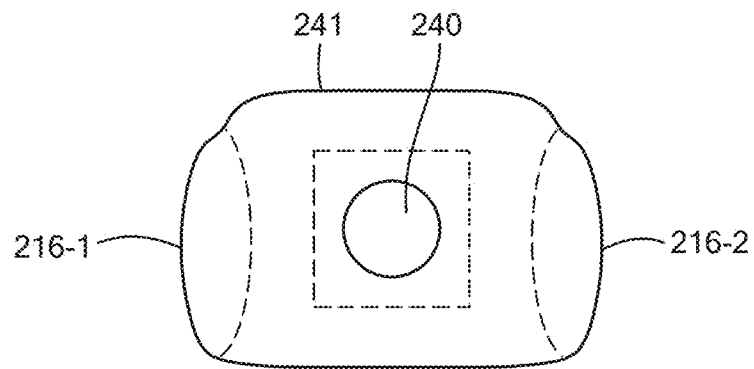
FIGS. 13A and 13B show top and side views, respectively, of an actuated switch on the device of FIGS. 10A-12.
Figure 13B:
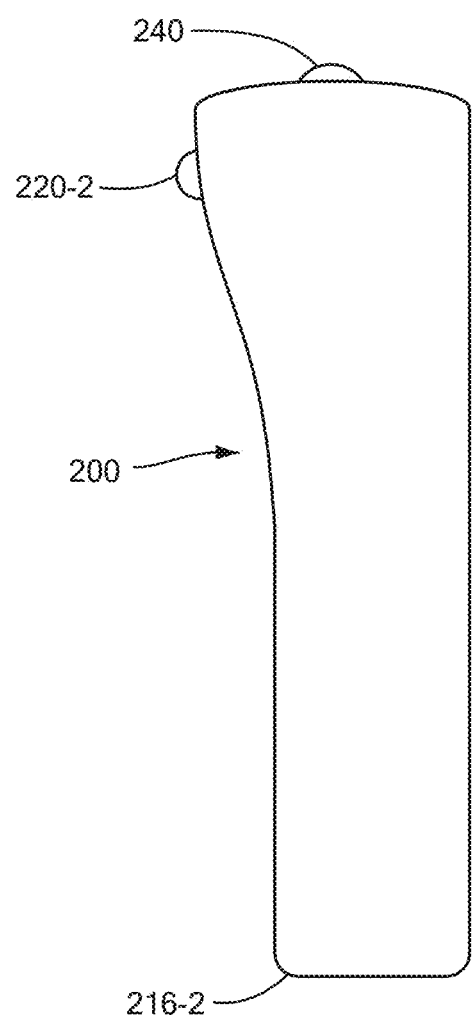

FIGS. 13A and 13B show top and side views, respectively, of an actuated switch on the device of FIGS. 10-12. Referring to FIGS. 10A-13B, a switch 240 is disposed on an upper surface of the enclosure 212 and is adapted for opening and closing the connection between the power supply and the lighting element for completing a circuit for energizing the lighting element 220. The switch 240 also comprises a waterproof seal between an actuated portion of the switch and the electrical connection, such that the actuated portion is responsive to external movement for opening and closing the connection for powering the lighting element 220.

The switch 240 may be formed as a deformable panel 241 defining the actuated portion of the switch, and operable as a push button through the deformable material. An actuator, such as a plunger on an interior side, is responsive to movement of the deformable panel for opening and closing the connection through physically manipulating electrical contacts to open and close the circuit. Other suitable switching approaches may be employed, such as through a relay or a delay that toggles operation after being depressed for several seconds. By concealing the physically disposed actuator (i.e. plunger, contact, etc.) behind a deformable panel that still allows actuator movement, the waterproof seal is maintained around the switch 240.

Figure 14A:
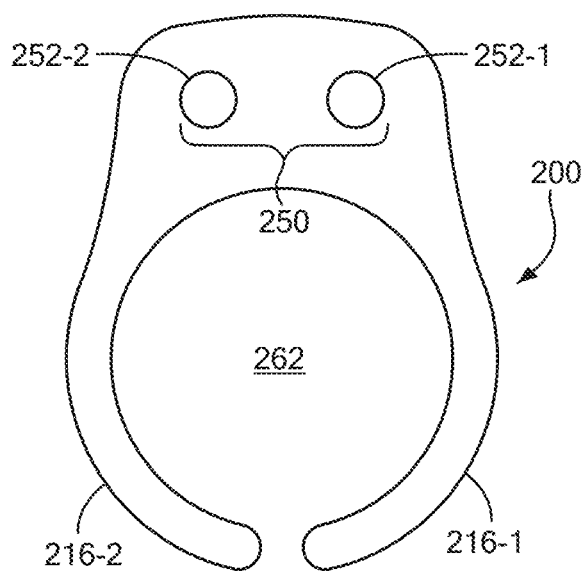
FIGS. 14A-14C show external conductors for recharging, a charger module, and an engaged charger module, respectively.
Figure 14B:
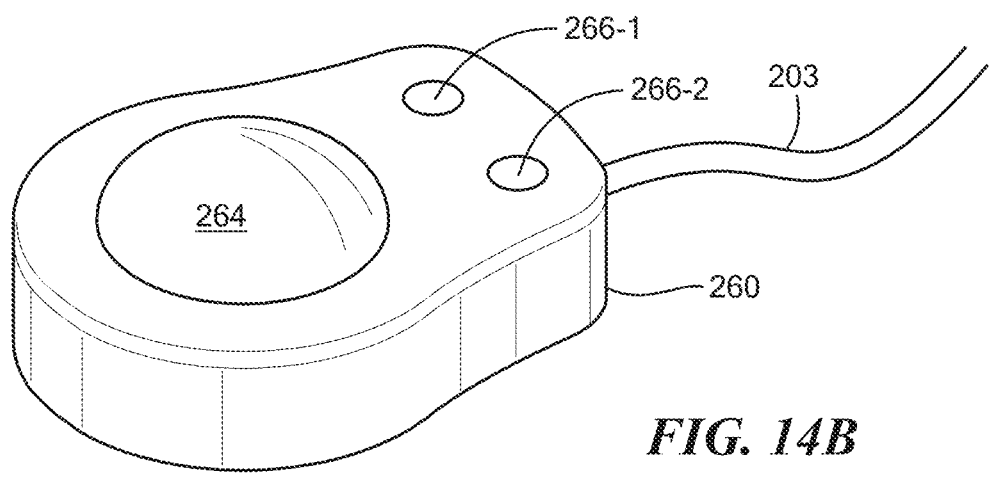
Figure 14C:
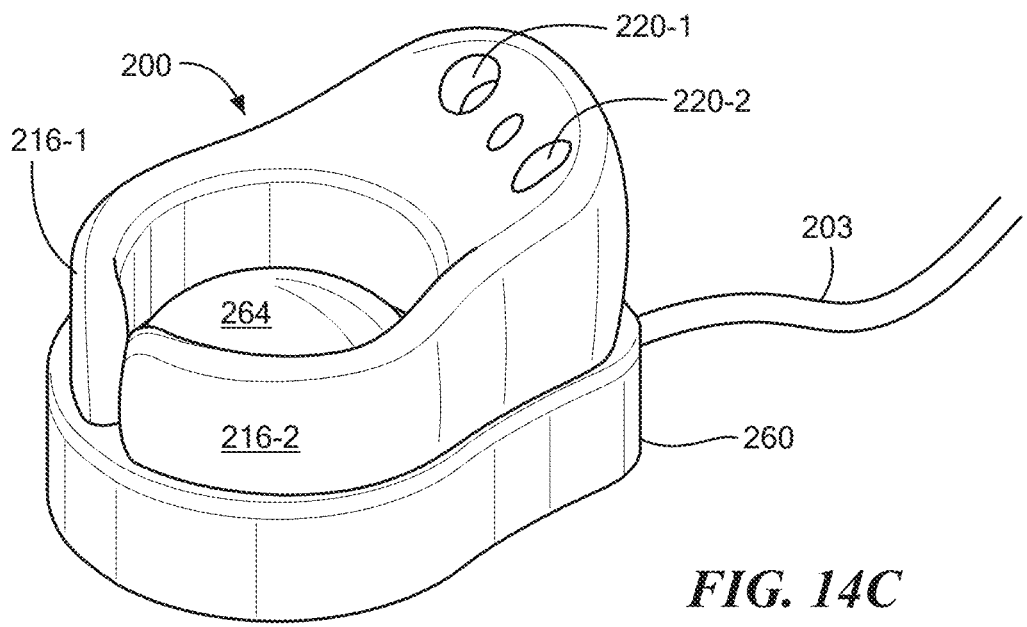

FIGS. 14A-14C show external conductors for recharging, a charger module, and an engaged charger module, respectively. Referring to FIGS. 10A-14C, a rear elevation in FIG. 14A shows a charge port 250 including two external conductors 252-1 ... 252-2 (252 generally). The conductors 252 provide electrical connections to the power supply 222.

In FIG. 14B, a charge module 260 is operable to connect to the device 200 for charging the power supply 250. The charge module 260 defines the electrical source for recharging, and receives power from a power cord 203. A pair of terminals 266-1 ... 266-2 (266 generally) on the charge module 260 provides charging power. A mating structure on the charge module 260 is disposed adjacent to the external conductors for positioning guidance of the terminals 266 by alignment with the annular frame 214. The pair of terminals 266-1 ... 266-2 is adapted for contacting a respective pair of the external conductors 252 on the enclosure upon alignment of the mating structure with the annular frame 214.

The annular design of the prongs 216, combine sizing and proportions to engage a human digit. In particular, the prongs 216 of the annular frame 214, when opposed by the concave side, define a roughly circular outline that can receive a similarly sized protrusion. In such a configuration, the annular frame 214 is adapted for mating or engagement with the charge module 260 having one or more terminals 266-1 ... 266-2 (266 generally), such that engagement with the charge module 260 disposes the terminals 266 on the charger into alignment with the external conductors 252 on the enclosure.

Water is generally problematic for any kind of electrical interface or circuit, as water itself is a conductor, in addition to the corrosion potential water creates. Accordingly, in contrast to the single use configuration, an electrical path is needed to allow charging from an external electrical source, yet ensure that the electrical path cannot be followed by water or fluid which could compromise the device 200 from infiltration into the void 232.

Well defined and disengageable electrical junctures are therefore called for. The charge module 260 has a protrusion 264 adjacent to the terminal 266, such that the protrusion 264 is adapted to engage the receptacle 262 for aligning the terminal 266 with a respective external conductor 252 on the enclosure 212. In the example of FIGS. 14A-15B, the protrusion 264 is a hemispherical portion or dome-like shape, and the quasi circular annular frame 214 has a slightly larger diameter for centering the prongs 216 around the protrusion.

Figure 15A:
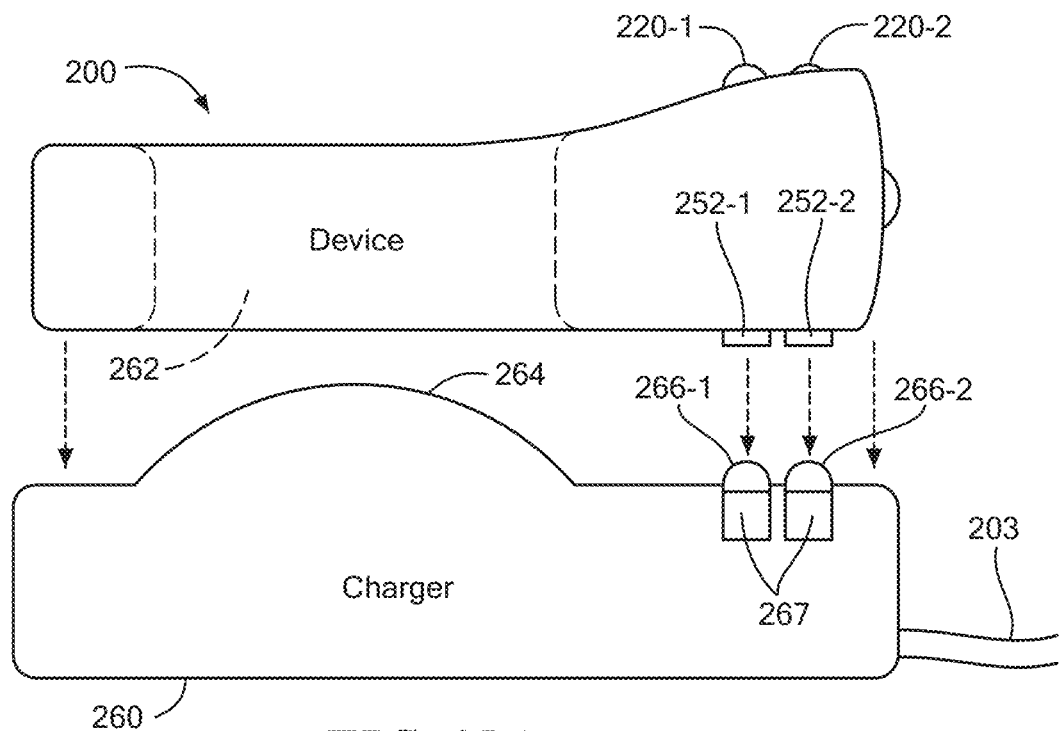
FIGS. 15A-15B shows a side view of the device of FIGS. 10A-14C engaging the charger of FIGS. 14B and 14C.
Figure 15B:
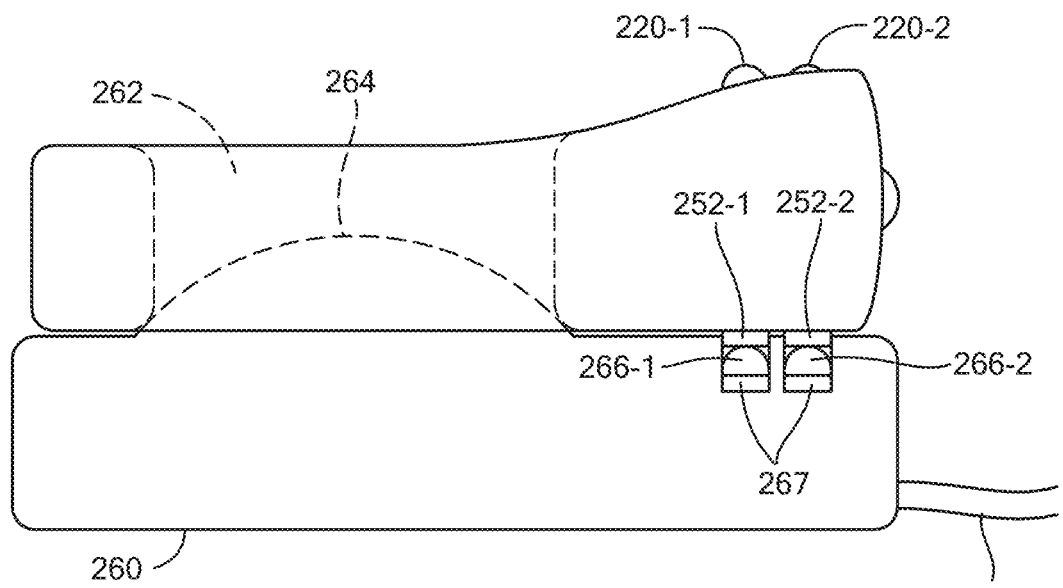

FIGS. 15A-B shows a side view of the device of FIGS. 10A-14C engaging the charger 260 of FIGS. 14B and 14C. Referring to FIGS. 14A-15B, the charge module 260 should establish a good electrical connection to the external conductors 252, to ensure a charge current can flow freely to the rechargeable battery 222. The external conductor 252 further comprises a biased contact 267, adapted for receiving a terminal 266 on the charge module 260. The biased contact imposes a resistive force against the terminal for maintaining electrical continuity during recharging. This may be achieved where the terminals 266 further comprises a pair of spring biased contacts 267, each adapted to engage a corresponding terminal 266 on the charge module 260 for completing a charging circuit with the rechargeable storage element. The external conductors 252 align with the contacts 267 for biased or spring loaded engagement upon a corresponding engagement of the charge module 260 with the annular frame 214, and in response, the terminals 266 retract slightly into the charger 260. Upwards biasing force from the retracted spring biased contacts maintains electrical continuity for reliable charging. In a particular configuration, such a spring biased connection may be obtained by a so-called "pogo pin" or similar construct. The sealed external conductors 252, along with the fused seam 234, therefore provides a waterproof seal between the lighting element, the external conductors and the enclosure for providing a waterproof device amenable to sterilization processes using heat and solvents or detergents.

While the system and methods defined herein have been particularly shown and described with references to embodiments thereof, it will be understood by those skilled in the art that various changes in form and details may be made therein without departing from the scope of the invention encompassed by the appended claims.

What is claimed is:

1. A method for providing finger-mounted illumination, comprising:
    providing an enclosure and an annular attachment;
    the annular attachment adapted to form a circumferential engagement with a human digit;
    the enclosure including:
        a lighting element for projecting light at least along an axis; and
        a power supply for powering the lighting element;
    establishing electrical communication between the power supply and the lighting element; and
    configuring the enclosure in an orientation around the human digit, with the lighting projecting towards the fingertip.

2. The method of claim 1 wherein the annular attachment defines at least a portion of the circumferential engagement.

3. The method of claim 1 wherein the annular attachment defines an annular concave recess having a size based on a human digit.

4. The method of claim 3 wherein the annular attachment is adapted to extend in a circumferential manner around the human digit, the lighting element projecting in a direction perpendicular to a direction of the extended annular attachment.

5. The method of claim 3 wherein the annular attachment is adapted for circumferential engagement of a human digit which extends through the annular concave recess.

6. A finger-mounted illumination device, comprising:
    a body having an enclosure and an annular attachment;
    the annular attachment extending in a plane from the enclosure, the annular attachment adapted to circumferentially engage a human digit with the lighting projecting towards a fingertip of the human digit;
    the enclosure including:
        a lighting element projecting light at least along an axis;
        a power supply for powering the lighting element.

7. The method of claim 6 wherein the annular attachment deforms in an adjustable manner for frictional engagement with human digits of varying circumferences.

8. The device of claim 6 wherein the lighting element defines a projection angle, the projection angle based an axis extending longitudinally through the engaged human digit for focusing on a distal end of the human digit.

9. The device of claim 6 wherein an anterior-posterior dimension of the annular attachment is shorter than an anterior-posterior dimension of the enclosure.

10. The device of claim 6 wherein at least one portion of the annular attachment includes a deformable material for providing a frictional engagement with the human digit, such that a circumference defined by the annular attachments is equal to or less than the circumference of the human digit.

11. The device of claim 6 wherein the annular attachment has a closure defining a circular shape adapted for slidable communication with the human digit.

12. The device of claim 6 further comprising a manual switch, the manual switch responsive to a user input for establishing the electrical communication between the power source and the lighting element.

13. The device of claim 6 wherein the body is adapted for underwater utilization by construction with waterproof materials and from sealing of the enclosure.

14. A method for providing task illumination using a finger-mounted illumination device having an annular attachment, comprising:
    disposing the annular attachment for circumferential frictional engagement with a human digit;
    closing an electrical circuit between an illumination source aligned with the human digit and a power supply for emitting outward directed light for utility lighting; and
    configuring the illumination source in an orientation around the human digit, with the light projecting towards a fingertip of the human digit.

15. The method of claim 14 wherein the human digit is a human finger.

16. The method of claim 14 further comprising directing the light in a direction perpendicular to the directions of the annular attachment.

17. A portable, self-contained personal lighting apparatus, comprising:

a body having an illumination source and a power supply for energizing the illumination source, the illumination source defined by one or more outward emitting lighting elements for utility lighting; and an attachment extending from the body, the attachment adapted to form an annular, concave form extending in a plane and adapted to circumscribe a human digit, the illumination source projecting light including at least along an axis focused on a distal region.

18. The apparatus of claim 17 wherein the outward emitting lighting element includes one or more light emitting diodes (LEDs) or lasers.

19. The apparatus of claim 17 further comprising a plurality of electrical contacts for closing a circuit between the illumination source and the power supply.

20. The apparatus of claim 17 wherein the body is constructed from materials adapted to withstand temperatures up to 200 degrees Fahrenheit and down to −90 degrees Fahrenheit.

21. The apparatus of claim 17 wherein the lighting elements include one or more light wavelengths, including but not limited to white light, red light, green light, yellow light, blue light, infrared light, reduced emission light for night vision, ultraviolet light, laser light.

22. The apparatus of claim 17 wherein the power supply is one or more batteries.

23. The method of claim 1 wherein the annular attachments extends in the plane.

\* \* \* \* \*